United States Patent [19]

Kluth et al.

[11] 4,348,909
[45] Sep. 14, 1982

[54] SAMPLING PROBE FOR TAKING PARTIAL LIQUID QUANTITIES FROM VARIOUS PHASES OF TWO IMMISCIBLE LIQUIDS

[75] Inventors: Manfred Kluth, Neuthard; Heinz Antoni, Eggenstein-Leopoldshafen; Werner Stich, Linkenheim-Hochstetten, all of Fed. Rep. of Germany

[73] Assignee: Kernforschungszentrum Karlsruhe GmbH, Karlsruhe, Fed. Rep. of Germany

[21] Appl. No.: 178,570

[22] Filed: Aug. 15, 1980

[30] Foreign Application Priority Data

Aug. 17, 1979 [DE] Fed. Rep. of Germany ....... 2933368

[51] Int. Cl.³ ............................................. G01N 1/20
[52] U.S. Cl. .............................. 73/863.21; 73/863.51; 73/863.86
[58] Field of Search ........... 73/863.21, 863.41, 863.51, 73/863.57, 863.86

[56] References Cited

U.S. PATENT DOCUMENTS 2,041,694  5/1936  Buckley ............................ 73/563.86
3,336,808  8/1967  Ryskamp ......................... 73/863.21

FOREIGN PATENT DOCUMENTS 697861  11/1979  U.S.S.R. ........................... 73/863.51

Primary Examiner—S. Clement Swisher
Attorney, Agent, or Firm—Spencer & Kaye

[57] ABSTRACT

A sampling probe for sampling partial quantities of liquid in a counter-current extraction column wherein the liquid has first and second immiscible phases moving in mutually opposite directions. The probe comprises an extraction tube having first and second radially opposing ports in its surface, the extraction tube being adapted for extending into the liquid within the column and positioned so that the first and second phases impinge upon the respective opposite portions of the extraction tube surface containing the radially opposing ports. A stopper formed of a material which promotes coalescence with respect to the first phase is fitted into one end of the extraction tube. The stopper has a cavity therein, and a plurality of apertures are located in the side of the stopper aligned with the portion of the extraction tube against which the first phase impinges. A conical valve formed of a material having substantially the same coalescing properties as the stopper material is slidably positioned within the extraction tube between the stopper and the other end of the tube. Channels located within the valve connect the cavity in the stopper with the interior of the extraction tube.

9 Claims, 5 Drawing Figures

Section A-A

Section B-B

Section C-C

Section D-D

SAMPLING PROBE FOR TAKING PARTIAL LIQUID QUANTITIES FROM VARIOUS PHASES OF TWO IMMISCIBLE LIQUIDS

BACKGROUND OF THE INVENTION

The present invention relates to a sampling probe for taking partial quantities of liquid from the various phases of two immiscible liquids. In particular, it relates to a probe for taking samples of organic, aqueous and mixed phases during reprocessing of nuclear fuels by the PUREX process wherein the organic and aqueous phases are charged in a pulsating column from the top or bottom in mutually opposite directions. The probe includes an extraction tube which extends into the liquid.

In accordance with the present invention, samples are taken from the continuous, dispersed and mixed phases of liquid mixtures of two immiscible liquids which are combined in a probe for use in pulsating column mixer settlers. Consequently, three types of samples must be extracted from the pulsating column: the continuous phase (aqueous), the dispersed phase (organic) and the mixed phase of the two preceding phases. All three must be taken pure, without decanting, inline from the pulsating column so that the extraction process can be monitored.

It has previously been customary to take separate samples of the individual phases by means of the funnel method or by means of a simple tube and with subsequent decanting. However, these methods do not permit a sharply defined separation of the continuous and dispersed phases. In prior art devices, a small amount of one phase will always be present as an impurity in the other phase resulting in subsequent exchanges of matter which falsify the sample. Due to this equalization of concentration, a true sample cannot be obtained which corresponds to the actual conditions in the column.

It is an object of the present invention to provide a sampling probe of the above-mentioned type which permits sharply defined separation of the continuous and dispersed phases to be obtained by the use of a simple component. It is important in this connection that an operator be able to extract the sample by remote control without contamination. It is also important that the probe be as small as possible and that it not unduly interfere with the process. Preferably, the probe should be round to simplify installation and, moreover, should be easily installed and removed during operation of the extraction column.

SUMMARY OF THE INVENTION

In accordance with the present invention, a sampling probe is provided for sampling partial quantities of liquid in a countercurrent extraction column wherein the liquid has first and second immiscible phases moving in mutually opposite directions. The probe comprises an extraction tube having first and second radially opposing ports in its surface, the extraction tube being adapted for extending into the liquid within the column and positioned so that the first and second phases impinge upon the respective opposite portions of the extraction tube surface containing the radially opposing ports. A stopper formed of a material which promotes coalescence with respect to the first phase is fitted into one end of the extraction tube. The stopper has a cavity therein, and a plurality of apertures are located in the side of the stopper aligned with the portion of the extraction tube against which the first phase impinges. A conical valve formed of a material having substantially the same coalescing properties as the stopper material is suitably positioned within the extraction tube between the stopper and the other end of the tube. Channels located within the valve connect the cavity in the stopper with the interior of the extraction tube.

More specifically, in a preferred embodiment of the invention, the first phase is an organic phase which ascends from the bottom of the column. A planar surface is disposed at the underside of the stopper and is oriented perpendicular to the direction of movement of the organic drops, the vertical connecting apertures to the cavity being disposed in the planar surface. The cavity is extended into a settling chamber disposed in the tube behind the stopper. This settling chamber is provided with lower and upper transverse bores, the channels in the valve, which are conically arranged, opening into this chamber.

An inner tube having a smaller diameter than the extraction tube is disposed within the extraction tube so that an annular space is provided between the inner surface of the extraction tube and the outer surface of the inner tube. The inner tube is inserted into the valve cone and its interior connected to the settling chamber by means of the connecting channels.

The extraction tube is made of a material which promotes coalescence with respect to the second phase, and is provided with inlet apertures for the second phase at the position of the extraction tube surface on which the second phase impinges. In a preferred embodiment, the second phase is an aqueous phase which descends from the top. Inlet apertures are disposed in the upper surface of the extraction tube in the region between the conical valve and the other end of the extraction tube. The conical valve, which seals the interior of the extraction tube at a valve seat, can be moved back and forth within the settling chamber so as to open and close the valve seat. When the valve is positioned in the valve seat, the conical portion of the valve closes the ports provided in the extraction tube. When the valve is displaced completely toward the stopper the ports are fully open to the annular space between the extraction and inner tubes.

An advantage of the probe is that a sample of the organic phase can be drawn properly without falsification and, therefore, true sampling results can be obtained with respect to the process taking place in the column. A particular advantage in this connection is that the probe is small, round and easy to install or remove. Another significant advantage is that only one probe is necessary for taking samples of the organic, aqueous and mixed phases, the three functions being performed in a particularly optimum manner.

DESCRIPTION OF THE PREFERRED EMBODIMENT

Figure 1:
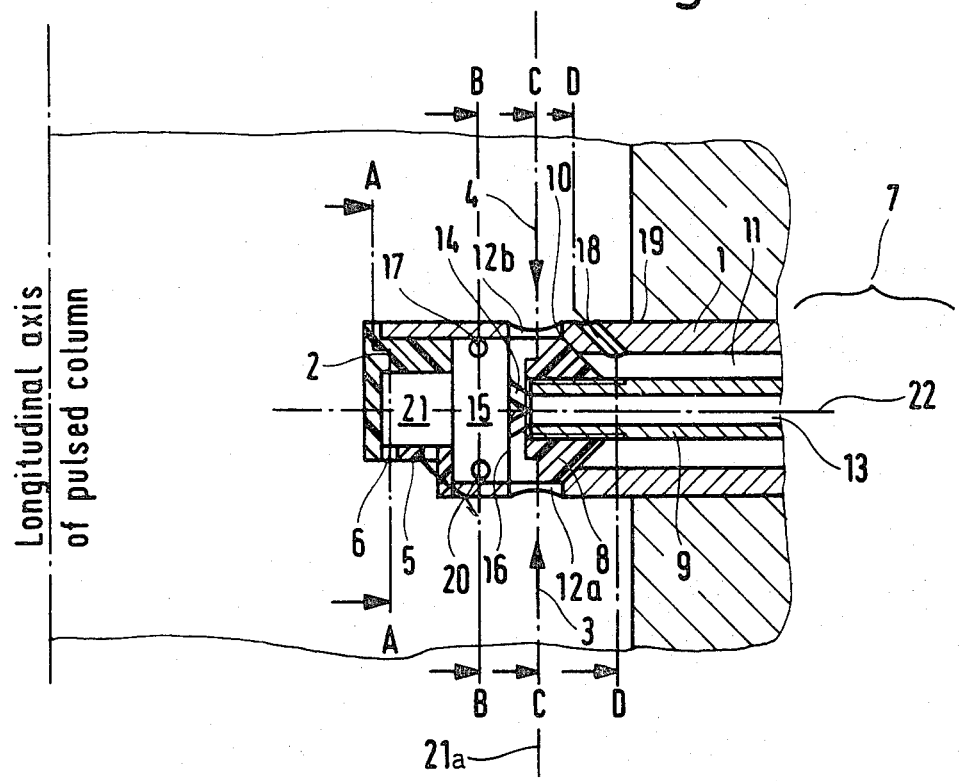
FIG. 1 is a cross-sectional view of a probe suitable for installation in a section of a counter-current extraction column.
Figure 2:
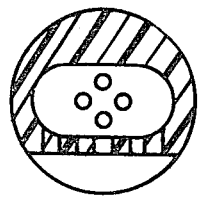
FIG. 2 is a section through the stopper.
Figure 3:
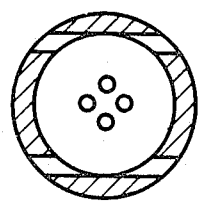
FIG. 3 is a section of the settling chamber.
Figure 4:
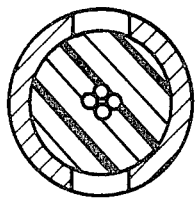
FIG. 4 is a section of the conical valve with the separation bores for the organic phase.
Figure 5:
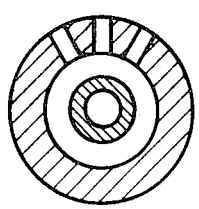
FIG. 5 is a section through the extraction-tube with the apertures for the continuous phase and the inner push pipe for the conical valve.

Referring to the drawing, the sampling probe comprises a stainless steel outer or extraction tube 1 sealed at one end by a polytetrafluoroethylene (PTFE) or polyethylene stopper 2. The other end 7 of the extraction tube is connected to a sample evaluation system (not shown). The tube 1 extends from one side horizontally into a process vessel such as a vertically arranged pulsating column for the liquid-liquid extraction during reprocessing of nuclear fuels according to the PUREX process. Such columns, which are well known and described, for example, in U.S. Pat. No. 3,869,374 issued Mar. 4, 1975, are charged from the top with the aqueous, i.e. heavy phase, and from the bottom in counter-current thereto with the organic, i.e. light phase. The aqueous phase contains the dissolved values and the organic phase forms the extraction agent, both phases being pulsated together. Thus, the organic phase in the column flows in the direction of the arrow 3 from the bottom against the extraction tube 1 and the aqueous phase flows from the top against the extraction tube in the direction of the arrow 4. The mixed phase consisting of both the organic and aqueous phases surrounds the extraction tube and, aside from the pulsation applied for drop formation, has no defined direction of flow.

Part of the stopper 2 is cut out at it's underside so that a planar face 5 is produced. The face 5 is perpendicular to the direction of movement 3 of the organic drops and is provided with a plurality of vertical apertures 6. These apertures lead into a cavity 21, cavity 21 opening into the settling chamber 15. A conical valve 8 made of PTFE or polyethylene is slidably positioned between the stopper 2 and the end 7 of the extraction tube 1. The valve 8 is seated on an inner tube 9 so that it is positioned within and concentric with the outer extraction tube 1. The conical valve 8 seals the extraction tube 1 along it's circumference and also seals the annular space 11 between the inside of the outer extraction tube 1 and the outside of the inner tube 9 at the valve seat 10. By moving the inner tube 9 in the horizontal direction toward the stopper 2, the conical valve is displaced to the left completely exposing identically-sized ports 12a, 12b centered on a vertical radial line 21a which is perpendicular to the longitudinal axis 22 of the probe.

The conical valve 8 is provided with three conically arranged channels 14 which lead to the interior 13 of the inner tube 9. These channels connect the settling chamber 15 between the stopper 2 and frontal face 16 of the valve 8 with the interior 13 of the inner tube 9. The settling chamber 15 is provided with upper transverse bores 17 and lower transverse bores 20. Transverse bores 17 and 20 are disposed horizontally through the outer tube 1 at it's upper and lower side midway between the end of the stopper 2 and the frontal face 16 of the conical valve 8. Additionally, three obliquely oriented inlet apertures 18 are provided on the upper side 19 of the outer extraction tube 1 to provide a connection between the annular space 11 formed by the inner tube 9 and the outside of the extraction tube.

The sampling probe makes it possible to extract the mixed, organic and aqueous phases separately from a quantity of liquid. The operation of the probe is as follows:

(a) Mixed Phase:

To sample the mixed phase, the valve 8 is moved to the left away from the seat 10. This permits the mixed phase to pass through the relatively large cross section of the two large ports 12a, 12b in the extraction tube 1 to the annular channel 11 from which it is conducted to a sample bottle through a suitable conduit system (not shown). The three inlet apertures 18 on the upper side 19 of the outer tube 1 do not play a significant part in the sampling of the mixed phase because the ratio of the area of the large ports 12a, 12b to the small apertures 18 is relatively large, on the order of 1:8.

(b) Aqueous Phase (continuous phase):

To sample the aqueous phase, the valve 8 is displaced to the right so that it presses against the seat 10 thereby closing the ports 12a and 12b. This permits the aqueous phase coming from the top from direction 4 to flow through the three apertures 18 on the upper portion 19 of the extraction tube surface into the annular space 11. The aqueous phase is conducted, as in the case of the mixed phase, to sample bottles through a system of conduits.

Penetration of the organic phase coming from the bottom from direction 3 into the apertures 18 is prevented by (1) the better hydrophilic (wetting) properties of the metallic material with respect to the aqueous phase than to the organic phase, thereby promoting coalescence, so that the organic phase runs alongside the tube, and (2) the position of the bores 18 on the side 19 of the outer extraction tube 1 opposite the drop impingment surface of the organic phase. The result is that the hydrophility causes the aqueous phase to pass more easily than the organic phase through the aperture 18 because the resistance to which the organic phase is subjected in moving through a 1 mm diameter bore is much higher. The basiic idea of the system is that only one phase can pass through bores of small diameter when it is able to wet the material forming these apertures; otherwise, it is pushed back into the mixed phase of the column.

(c) Organic Phase (Dispersed Phase):

To sample the organic phase, the conical valve 8 is also displaced to the right so that it presses against the seat 10, as in sampling the aqueous phase. The organic drops which rise in the continuous phase in the direction 3 impinge on the planar surface 5 of the stopper 2 at the end of the outer extraction tube 1. Some of these drops flow together at the PTFE or polyethylene stopper 2 which acts to promote coalescence and enter through apertures 6 into the settling chamber 15 between the stopper 2 and conical valve 8.

In settling chamber 15, a further separation of the two phases occurs. The aqueous phase leaves the probe through the two lower transverse bores 20, the organic droplets being retained. The surplus organic phase leaves the settling chamber 15 through the upper transverse bores 17 to assure continuous steady flow which prevents entry of the aqueous phase from the top, these elements constituting the first barrier against the aqueous phase. The four conically arranged channels 14 in the frontal face 16 of the conical valve 8 effect, again because of the coalescence effect of the PTFE or polyethylene for the organic phase, the final separation between the organic and aqueous phases and constitute the second barrier for the aqueous phase. The organic phase flows through the interior 13 of the inner tube 9 into a sampling bottle.

The settling chamber 15 acts like a decanter in or to separate the light from the heavy phase, and so the bouyancy forces the surplus organic phase to leave the settling chamber through the two upper transverse bores. The phase ratio outside in the column is about 1:10 and, inside the chamber 15 about 1:1 or lower, so that the amount of organic phase for the second PTFE-separator is high and the final separation of the two phases is easy.

For systems with a reversed phase relationship, organic continuous and aqueous dispersed, the probe may be installed in a position rotated by 180° and the components which promote coalescence are made of other substances which are adapted to the materials in question. For example, the extraction tube 1 could be made of PTFE or Polyethylene, and the stopper 2 and conical valve 8 of stainless steel.

It will be understood that the above description of the present invention is susceptible to various modifications, changes and adaptations, and the same are intended to be comprehended within the meaning and range of equivalents of the appended claims.

What is claimed is:

1. A sampling probe for sampling partial quantities of liquid in a countercurrent extraction column wherein said liquid has first and second immiscible phases moving in mutually opposite directions, said probe comprising:
   (a) an extraction tube having first and second radially opposed ports in the surface thereof, said extraction tube being adapted for extending into the liquid within said column and positioned so that said first and second phases impinge upon the respective opposite portions of the extraction tube surface containing said radially opposing ports;
   (b) a stopper formed of a material which promotes coalescence with respect to said first phase fitted into one end of said extraction tube, said stopper having a cavity therein and a plurality of apertures located in the side of said stopper aligned with the portion of said extraction tube aganst which said first phase impinges; and
   (c) a conical valve formed of a material having substantially the same coalescing properties as said stopper material slidably positioned within said extraction tube between said stopper and the other end of said tube, said valve having channels therein for connecting the cavity in said stopper with the interior of said extraction tube.

2. A probe as defined in claim 1 wherein said first phase is an organic phase which ascends from the bottom of said extraction column; said stopper is provided with a planar face oriented perpendicularly to the direction of movement of the drops of said organic phase, said plurality of apertures in said stopper being located in said planar face and perpendicular thereto; and which further comprises a settling chamber disposed within said extraction tube between said stopper and said valve, said settling chamber including lower and upper transverse bores, the channels in said valve being conically arranged and opening into said settling chamber.

3. A probe as defined in claim 2 which further comprises an inner tube concentrically situated within said extraction tube so as to form an annular space therebetween, said inner tube being inserted within said conical valve and it's interior connected to said settling chamber by said conically arranged channels.

4. A probe as defined in claim 1 or 2 wherein said extraction tube is provided with a plurality of obliquely oriented inlet apertures in the portion of its surface upon which said second phase impinges, said extraction tube being formed of a material which promotes coalescence with respect to said second phase.

5. A probe as defined in claim 4 wherein said second phase is an aqueous phase which descends from the top of said extraction column, and wherein said inlet apertures are located in the upper portion of the surface of said extraction column in the region between said conical valve and the other end of said extraction tube.

6. A probe as defined in claim 3 wherein said extraction tube is provided with a plurality of obliquely oriented inlet apertures in the portion of its surface upon which said second phase impinges, said extraction tube being formed of a material which promotes coalescence with respect to said second phase.

7. A probe as defined in claim 6 wherein said extraction tube is provided with a peripheral valve seat adjacent said radially opposed ports, said conical valve sealing the annular space between said extraction and inner tubes by pressing against said valve seat in a first position thereby closing said ports in said extraction tube, and connecting said annular space to said ports when translated toward said stopper to a second position within said settling chamber.

8. A probe as defined in claim 7 wherein said conical valve is displaceable toward said stopper until said ports are fully open to said annular space between said extraction tube and said inner tube.

9. A probe as defined in claim 6 wherein said second phase is an aqueous phase which descends from the top of said extraction column, and wherein said inlet apertures are located in the upper portion of the surface of said extraction column in the region between said conical valve and the other end of said extraction tube.

* * * * *